| United States Patent [19] | [11] Patent Number: 5,053,574 |
|---|---|
| Tsutsui et al. | [45] Date of Patent: Oct. 1, 1991 |

[54] HYDRODEALKYLATION OF ALKYLAROMATIC COMPOUNDS

[75] Inventors: Toshio Tsutsui, Kashiwa; Osamu Kubota, Sodegaura, both of Japan

[73] Assignee: Fuji Oil Company, Ltd., Tokyo, Japan

[21] Appl. No.: 522,365

[22] Filed: May 11, 1990

[30] Foreign Application Priority Data

May 12, 1989 [JP] Japan .................... 1-119877

[51] Int. Cl.$^5$ ............................ C07C 4/12; C07C 4/18
[52] U.S. Cl. .................................. 585/488; 502/182; 585/486
[58] Field of Search ................ 502/182; 585/485, 486, 585/488

[56] References Cited

U.S. PATENT DOCUMENTS 3,360,134 12/1967 Puller .................................. 585/488
4,247,730 1/1981 Brunelle ........................... 585/488
4,598,060 7/1986 Schoenthal et al. .............. 585/486

FOREIGN PATENT DOCUMENTS 7167928 4/1981 Japan .............................. 585/486

*Primary Examiner*—Asok Pal
*Assistant Examiner*—P. N. Achutamurthy
*Attorney, Agent, or Firm*—Oblon, Spivak, McClelland, Maier & Neustadt

[57] ABSTRACT

A catalyst for hydrodealkylation of alkylaromatic compounds which comprises porous alumina particles with coke deposited thereon in the pores, said alumina particles having a pore volume of 0.1 to 1.5 cm$^3$/g and a specific surface area of 5 to 500 m$^2$/g, the quantity of said coke being 1 to 30% by weight of said alumina particles, and the pore volume and the specific surface area of said catalyst being 0.05 to 1.5 cm$^3$/g and 1 to 500 m$^2$/g, respectively.

7 Claims, No Drawings

HYDRODEALKYLATION OF ALKYLAROMATIC COMPOUNDS

BACKGROUND OF THE INVENTION

As the method of hydrodealkylation of alkylaromatic compounds to produce more useful aromatic compounds, both thermal and catalytic processes have been utilized so far.

In the thermal processes, it is usually required to conduct the reaction under such a severe condition as a temperature higher than 700° C. and a high pressure. This leads to the necessity of using high temperature endurable, expensive materials, and/or of being equipped with sophisticated quench-means to prevent the temperature rise in the reactor due to the exothermic hydrodealkylation reaction, which requires difficult operation for optimum quenching.

In the catalytic processes, the hydrodealkylation reaction is conducted at a temperature lower than 700° C. by the use of catalysts. However, as far as the inventors of this invention know, the catalytic processes which are known heretofore have various problems or difficulties as described below.

Hydrodealkylation with a catalyst such as chromia or molybdenum oxide supported on alumina or others has been utilized as an industrial process of toluene hydrodealkylation. However, the activity of these catalysts is not always high enough, and, if the reaction temperature or hydrogen pressure is increased in order to increase the conversion, side reactions such as hydrocracking of aromatic ring are also promoted.

It is also known to use the catalyst of transitional metal such as Rh, Pt and Ir supported on alumina or others for catalytic hydrodealkylation. However, these metals are not only very expensive and therefore uneconomical, but the activity is often unstable. Furthermore, these metals have the problem of severe deactivation due to poisoning by sulfur contained in feed oil or deposition of coke.

Although solid acid such as silica-alumina and zeolite is also known as a hydrodealkylation catalyst, there are problems that the activity is not high enough and side reactions such as disproportionation of alkylaromatic compounds and coke formation are remarkable.

Alumina can be used as a catalyst for the hydrodealkylation, but the catalytic activity is low though the selectivity of the reaction is high.

Hydrodealkylation process with activated carbon is known by Japanese Patent Application Laid-Open Specification No. 51-23228. However, because activated carbon adsorbs reactant and product compounds too strongly, large amount of coke is formed during the reaction, which results in low selectivity of the hydrodealkylation reaction and lowering of reactivity in a short period of the reaction.

SUMMARY OF THE INVENTION

The present invention in one aspect thereof provides a catalyst for hydrodealkylation of alkylaromatic compounds which comprises porous alumina particles with coke deposited thereon in the pores, said alumina particles having a pore volume of 0.1 to 1.5 cm$^3$/g and a specific surface area of 5 to 500 m$^2$/g, the quantity of said coke being 1 to 30% by weight of said alumina particles, and the pore volume and the specific surface area of said catalyst being 0.05 to 1.5 cm$^3$/g and 1 to 500 m$^2$/g, respectively.

The catalyst according to this invention can be manufactured with ease by conducting decomposition of a hydrocarbon compound such as, for example, thermal cracking or hydrodealkylation (when the hydrocarbon compound is an alkylaromatic compound) thereof in the presence of alumina particles. The activity of the catalyst is further enhanced by subsequent treating in the atmosphere comprising molecular oxygen and/or steam at a temperature of 600° to 1000° C.

The present invention, in another aspect, provides a process for hydrodealkylation of alkylaromatic hydrocarbons which comprises contacting an alkylaromatic compound with a catalyst as claimed in claim 1 under a hydrogen partial pressure of 1 to 50 kg/cm$^2$ and at a temperature of 450° to 700° C.

According to this invention, it is made possible to remarkably enhance the hydrodealkylation activity of porous alumina particles, which inherently have a high selectivity but may not have a high activity when used for the hydrodealkylation, without causing lowering of selectivity or of reactivity in a short reaction period which are often observed on an activated carbon catalyst, by modifying the porous alumina particles so that they have coke deposited thereon.

DETAILED DESCRIPTION OF THE PREFERRED EMBODIMENT

[I] Catalyst particles

Carrier alumina particles

Catalyst particles for hydrodealkylation according to this invention comprises porous alumina particles with coke deposited thereon in the pores. Although these alumina particles themselves possess some but not high enough activity for hydrodealkylation, the alumina particles without coke deposited thereon are called carrier hereinafter in order to distinguish them from the catalyst particles according to the invention i.e. alumina particles with coke deposited thereon in the pores.

The alumina particles to be used as a carrier in this invention are those having pore volume of 0.1 to 1.5 cm$^3$/g, preferably 0.2 to 1.2 cm$^3$/g, and specific surface area of 5 to 500 m$^2$/g, preferably 10 to 350 m$^2$/g. The wording "alumina" herein used includes pure Al$_2$O$_3$ and Al$_2$O$_3$ based solid materials which comprise Al$_2$O$_3$ as the major component, and therefore is clearly distinguished from such solid acid substance as silica-alumina or zeolite which are made of silica as the major component.

Representative examples of alumina thus defined are alumina in various state such as, for example, γ-alumina. The alumina according to this invention can contain other components as far as Al$_2$O$_3$ is the major component, the maximum content of the other components being about 30%. The carrier porous alumina particles according to this invention may therefore contain, in addition to Al$_2$O$_3$, such components to increase thermal stability of the particles as silica, titania, magnesia, oxides of Ba, La or others, P and others.

The porous alumina particles for use as a carrier in the catalyst according to this invention can contain metal component as an active component for hydrogenation or hydrodealkylation such as, for example, Ni, V, Pt, Rh, Co, Cr, Mo or others in the form of metal, oxide, sulfide, salt or organic compound. Also in such cases, hydrodealkylation reactivity of the particles can be further enhanced by the coke deposited thereon according to this invention.

Manufacture of catalyst

Porous alumina particles with coke deposited thereon in the pores according to this invention can be manufactured in such a way that coke is deposited in the pores of the carrier porous alumina particles, preferably in a fluidized bed, by conducting cracking of hydrocarbon compound, for example by conducting thermal cracking of hydrocarbon compound or like, or by conducting hydrodealkylation of alkylaromatic compound or alkylaromatic compound containing oil over the carrier porous alumina particles. By treating with molecular oxygen containing gas and/or steam at a temperature of 600° to 1000° C., the reactivity of the particles is further enhanced.

As the hydrocarbon mentioned above, gaseous hydrocarbons such as, for example methane, ethane or others, or liquid hydrocarbon of low boiling point such as, for example naphtha, gas oil or others may be used, but preferably used are liquid hydrocarbons of a high boiling point of, for example, not less than 3% by weight in CCR (Conradson Carbon Residue) such as crude oil, distillation residue thereof, pitch or coal tar, or liquid oil of high boiling point including aromatic compound, especially polyaromatic compound with two or more aromatic rings (for example, naphthalene- or phenanthrene-compound). The alkylaromatic compounds mentioned above include, for example, monoaromatic or polyaromatic compounds substituted by at least one alkyl-group such as toluene, indene, methylnaphthalene, and others. The liquid oil including alkylaromatic compound is, for example, catalytic cracking cycle oil, oil from catalytic reformer, coal tar, oil or tar as a by-product of naphtha cracking, oil produced by coal liquefaction, or others.

Through such a reaction as thermal cracking of hydrocarbons or hydrodealkylation of alkylaromatics or alkylaromatics-containing oil in the presence of porous alumina particles, coke is deposited mainly in the pores of the porous alumina particles. And, preferably, the porous alumina particles with coke deposited thereon are treated at 600° to 1000° C. with molecular oxygen-containing gas, for example, air, molecular oxygen, molecular oxygen-containing flue gas, or others, and/or steam. The treating time is between several seconds and several ten hours. By selecting quantity of deposited coke in the coke deposition step or treating condition of the particles with coke deposited thereon in the treating step, porous alumina particles with coke deposited thereon in the pores in a quantity of 1 to 30% by weight of the alumina particles are obtained. If the quantity of the coke deposited in the pores of the alumina particles is higher than 30% by weight of the alumina particles, such undesirable features may arise to the particles that pore volume and specific surface area of the alumina particles become too small, apparent bed density of the alumina particles becomes too large, and therefore reactivity and fluidity of the alumina particles are insufficient. On the other hand, if the quantity of the coke is lower than 1% by weight of the alumina particles, the effect of deposited coke may not be sufficient.

Thus obtained porous alumina particles with coke deposited thereon in the pores have somewhat smaller pore volume of 0.05 to 1.2 cm$^3$/g and about the same or somewhat smaller specific surface area of 1 to 500 m$^2$/g in comparison with those of the carrier alumina particles without coke.

In case that the porous alumina particles contain a metal component having hydrodealkylation activity, such modified alumina particles can be prepared by a suitable or conventional method such as, for example, impregnation or coprecipitation method. As the impregnation method, for example, there are various methods which include: a method in which the porous alumina particles are impregnated with a solution of a salt of the metal component, and are then treated by usual way, i.e. by all or part of the procedure of drying, thermal decomposition, reduction with hydrogen, and others; or a method in which the porous alumina particles are impregnated with an organic compound of the metal component dissolved in a hydrocarbon oil or with an oil containing as impurities a metal component such as Ni, V and others, for example crude oil, distillation residue thereof such as atmospheric or vacuum residue, or pitch, and are then subjected to thermal cracking or decomposition of the impregnated material. The content of the metal component is usually between about 0.1 and about 30% by weight of Al$_2$O$_3$. The above mentioned introduction of the metal component can be carried out before, during or after the deposition of coke in the pores of the alumina particles.

In the case that the porous alumina particles are those which contain the metal component as described above, the treating of the particles with molecular oxygen containing gas and/or steam at 600° to 1000° C. gives especially desirable effect to the particles. That is because the metal component on the particles is often covered or masked by coke when coke deposition treatment is carried out after impregnation of the metal component and hence the desired effect of the metal component is suppressed.

[II] Hydrodealkylation

Hydrodealkylation according to this invention is usually carried out at a temperature of 450° to 700° C., preferably 500° to 650° C., under a hydrogen partial pressure of 1 to 50 kg/cm$^2$, preferably 2 to 30 kg/cm$^2$.

Feedstock for the hydrodealkylation is alkylaromatic compound such as toluene, xylene, tri-methylbenzene, indene, methylnaphthalene, di-methylnaphthalene or others, or alkylaromatics-containing oil such as catalytic cracking cycle oil, oil from a catalytic reformer, coal tar, by-product oil from naphtha cracker, coal-liquefied oil or others. These feedstocks may contain S-, N- or O-containing organic compound such as benzothiophene, quinoline, phenol, dibenzofuran or others.

"Alkylaromatic compound" in the expression "alkylaromatic compound is contacted with a catalyst" in this invention includes alkylaromatic compound in various states as mentioned above.

According to this invention, it is possible by hydrodealkylation of the feedstock mentioned above to produce an aromatic compound such as benzene, naphthalene or others or an alkylaromatic compound with less carbon atoms in the alkyl groups, for example methylnaphthalene, than that of feedstock alkylaromatic compound at a high yield and selectivity. Especially, lowering of selectivity due to coke formation in a large quantity during the hydrodealkylation which is often observed in hydrodealkylation on an activated carbon catalyst may not arise.

As the reaction apparatus to be used for the hydrodealkylation according to this invention, fluidized bed apparatus is preferable. In case that fluidized bed apparatus is used, the porous alumina particles preferably have weight-mean diameter of 25 to 250 μm, apparent bed density of 0.3 to 1.5 g/cm$^3$ and substantially spherical shape. The carrier alumina particles can be manufactured to have above mentioned properties by usual method, for example, by spray-drying method. It is needless to say that the hydrodealkylation according to this invention can be carried out in an apparatus of a catalyst bed other than fluidized bed such as, for example, an apparatus of a fixed bed or a moving bed.

As an embodiment of this invention, an apparatus comprising two fluidized beds can be used, with which the hydrodealkylation reaction of an alkylaromatic compound or feed oil containing alkylaromatic compound is conducted in one fluidized bed, porous alumina particles with coke deposited thereon during the hydrodealkylation reaction are treated with molecular oxygen-containing gas and/or steam in the other fluidized bed, and the porous alumina particles are recirculated between the both fluidized beds. In this way, the method of this invention can be carried out continuously.

EXAMPLE 1

Hydrodealkylation reaction was conducted under the condition described as follows.

(1) Carrier particles 4 liters of porous alumina particles of a pore volume of 0.96 cm$^3$/g, a specific surface area of 240 m$^2$/g, a weight-mean particle size 70 μm and an apparent bed density of 0.45 g/cm$^3$, and of a substantially spherical shape were used.

(2) Experimental apparatus

A column of 8 cm in inner diameter was used as the reactor apparatus.

(3) Preparation of catalyst particles 4 liters of the porous alumina particles were charged in the reactor and fluidized by nitrogen in the rate of 1.0 Nm$^3$/h at 450° C. under normal pressure. Coal tar which contains no metal component was introduced to the fluidized bed for 2 hours in the rate of 1.2 kg/h and was subjected to thermal cracking. As a result, alumina particles with coke deposited thereon in the pores in the quantity of 28.6% by weight of the alumina particles were obtained.

Then, in the same apparatus, the particles were treated with air in the rate of 900N lit./h for about 5 hours at 720° C. under normal pressure, and alumina particles with coke deposited thereon in the pores in the quantity of 8.1% by weight of the alumina particles were obtained.

In the similar way, alumina particles with coke deposited thereon in the pores in the quantity of 1.5% and 27.4% by weight of the alumina particles were prepared respectively, with a feed period of coal tar and a treating period with air changed.

(4) Reaction experiments

Hydrodealkylation experiments of β-methylnaphthalene were carried out wherein the alumina particles with coke deposited thereon in the pores described above, porous alumina particles without coke, coke particles substantially without pore (fluid cokes), and activated carbon particles, respectively, were used.

Experimental conditions were as follows: pressure of 8 atm, temperature of 600° C. and 650° C. H$_2$ rate of about 4.5 Nm$^3$/h, superficial gas velocity of about 10 cm/s, feed (β-methylnaphthalene)rate of 1.2 kg/h.

Results obtained are shown in Table 1 and 2. When the alumina particles with coke deposited thereon in the pores according to this invention are used, a very high yield and selectivity of hydrodealkylation were obtained, compared with those wherein porous alumina particles without coke were used.

Such high reactivity and selectivity cannot be obtained by merely using coke particles (see fluid cokes in Table 1). Lowering of selectivity due to a large amount of coke formation and excessive gas generation because of overcracking, which may be observed on the activated carbon, was not essentially found with the alumina particles with coke deposited thereon in the pores according to this invention.

TABLE 1

| Particles | Alumina particles with coke deposited thereon | | | Alumina particles | Fluid cokes |
|---|---|---|---|---|---|
| Reaction temperature: 600° C. | | | | | |
| Coke content, wt % | 1.5 | 8.1 | 27.4 | 0 | 100 |
| Naphthalene yield, mole % | 40.4 | 41.7 | 39.8 | 18.6 | 15.5 |
| Coke yield, wt % | 0.3 | 0.3 | 0.4 | 0.7 | 0.2 |
| Excessive gas yield, wt % | 0.8 | 0.8 | 0.9 | 0.6 | 2.3 |
| Naphthalene selectivity, mole % | 97.3 | 97.4 | 96.8 | 93.5 | 86.1 |

TABLE 2

| Particles | Alumina particles with coke deposited thereon | Alumina particles | Activated carbon |
|---|---|---|---|
| Reaction temperature: 650° C. | | | |
| Coke content, wt % | 3.2 | 0 | 100 |
| Naphthalene yield, mole % | 72.6 | 59.4 | 63.1 |
| Coke yield, wt % | 2.8 | 2.3 | 28.8 |
| Excessive gas yield, wt % | 2.7 | 2.5 | 7.6 |
| Naphthalene selectivity, mole % | 93.0 | 92.5 | 63.4 |

Excessive gas yield = Gas yield − Theoretical yield of methane by hydrodealkylation

EXAMPLE 2

The reactor column used in Example 1 was combined with another column of 2.8 cm in inner diameter so that catalyst particles can be recycled between the two columns. The second column was for re-activating the catalyst particles used in the first column.

11 liters of the same porous alumina particles as used in Example 1 were used in this experiment.

Hydrodealkylation of β-methylnaphthalene of the feed rate 3 kg/h was carried out in the first column at 600° C. under the pressure of 8 atm with hydrogen of about 7 Nm$^3$/h To the second column, about 0.9 Nm$^3$/h of nitrogen gas was introduced at initial stage, and the bed was maintained under nearly the same condition of pressure and temperature, then recirculation of the porous alumina particles was started.

In about 6 hours, the feed gas for the second column was changed to the mixture of 0.55 Nm$^3$/h of diluted air which was diluted with nitrogen to contain oxygen in 7.2 volume % and about 130 g/h of steam, and the temperature in the second column was adjusted and maintained at 720° C.

Under these conditions, the hydrodealkylation reaction of β-methylnaphthalene in the first column and the treating of the coke containing alumina particles, the coke of which was deposited and accumulated in the pores during the hydrodealkylation of the β-methylnaphthalene, in the second column were continuously carried out. In about 2 hours, a steady state in which coke content of the particles was kept at about 3.1% by weight was reached. The result of the hydrodealkylation reaction was as shown in Table 3.

TABLE 3

| Naphthalene Yield, mole % | 59.2 |
|---|---|
| Naphthalene Selectivity, mole % | 96.6 |

EXAMPLE 3

The same apparatus comprising two columns as used in Example 2 was used. 10 liters of alumina particles carrying 2.8% by weight of vanadium were used as catalyst particles. The alumina particles carrying vanadium were prepared as follows. In 3800 g of aqueous solution of 200 g of oxalic acid, 290 g of ammonium metavanadate was dissolved. The same porous alumina particles as used in Example 1 were then impregnated with the solution thus produced, and were dried in air at 105° C. for 1 hour.

These particles were charged in the first column and treated at 250° C. with air for 1 hour, and then reduced with hydrogen at 450° C. for 3 hours and at 600° C. for 1 hour.

Under the pressure of 8 atm, about 7 Nm³/h of hydrogen and 3 kg/h or β-methylnaphthalene as a feedstock were introduced into the first column, and the hydrodealkylation reaction was conducted at 600° C. At initial stage, about 0.9 Nm³/h of nitrogen was introduced to the second column which was kept under nearly the same condition of pressure and temperature as that in the first column, and then the recirculation of the catalyst particles between the both reaction and treating apparatus, two columns, was started.

In about 5 hours, the feed gas to the second column was changed to the mixture of about 0.77 Nm³/h of air and about 540 g/h of steam, and the temperature in the second column was adjusted and maintained at 770° C. Under this condition, the hydrodealkylation of β-methylnaphthalene in the first column and the treating of the coke-containing catalyst particles in the second column, the coke of which was deposited and accumulated in the pores during the hydrodealkylation, were continuously carried out. In about 2 hours, a steady state was reached, in which the coke content of the catalyst particles was kept at about 9.1% by weight. The result of the reaction was as shown in Table 4. In the table, the result with the catalyst particles of zero coke content is also shown for comparison.

TABLE 4

| | Example | Comparative example |
|---|---|---|
| Catalyst particles | Alumina particles containing 2.8% by weight of vanadium | |
| Coke content, wt % | 9.1 | 0 |
| Naphthalene yield, mole % | 72.5 | 56.1 |
| Naphthalene selectivity, | 93.5 | 93.3 |

TABLE 4-continued

| | Example | Comparative example |
|---|---|---|
| mole % | | |

EXAMPLE 4

Experimental apparatus

The same fluidized bed apparatus as used in Example 1.

Catalyst particles

With 4 liters of the same porous alumina as used in Example 1, hydrodealkylation of β-methylnaphthalene was carried out under hydrogen atmosphere at 650° C. As a result, alumina particles with coke deposited thereon in the pores in quantity of 2.2% by weight were obtained. These particles were used as the catalyst particles. Experimental conditions:

Reaction temperature at 650° C., hydrogen partial pressure at 7.8 atm, and β-methylnaphthalene feed rate at 1.2 kg/h.

Results of the experiment

Results obtained are shown in Table 5. In the table, comparative results are also shown, which were obtained by an experiment with porous alumina particles with no coke under the same reaction condition. It is shown that both naphthalene yield and selectivity are higher for alumina particles with coke deposited thereon in the pores than for alumina particles without coke.

TABLE 5

| | Example 5 | Comparative example |
|---|---|---|
| Particles | Alumina particles containing coke | Alumina particles |
| Coke content, wt % | 2.2 | 0 |
| Naphthalene yield, mol % | 59.4 | 52.3 |
| Naphthalene selectivity, mole % | 94.6 | 93.7 |

EXAMPLE 5

4 liters of substantially spherical, porous alumina particles with a pore volume of 0.39 cm³/g, a specific surface area of 96 m²/g, a weight-mean particle diameter 76 μm and an apparent bed density 0.83 g/cm³ were used, and particles with coke deposited thereon in the pores in quantity of 35% by weight of the alumina particles were prepared by the similar way as in Example 1.

Using thus obtained particles in the same fluidized bed apparatus as used in Example 1, hydrodealkylation of coal tar was conducted under a hydrogen partial pressure of 8 atm at 650° C. In about 15 minutes after the start of the reaction experiment, fluidized state of the particles became markedly impaired, and further continuation of the experiment could not be possible. It was thought that too large amount of coke initially held in the pores of the alumina particles caused the plugging of the pores of the alumina particles when further coke was deposited during the hydrodealkylation, and that consequently the particles stuck to each other with liquid coal tar which could not be absorbed into the pores whereby no fluidization was possible.

What is claimed is:

1. A process for hydrodealkylation of alkylaromatic hydrocarbons which comprises contacting an alkylaromatic compound with a catalyst which comprises porous alumina particles with coke deposited thereon in the pores, said alumina particles having a pore volume of 0.1 to 1.5 cm$^3$/g and a specific surface area of 5 to 500 m$^2$/g, the quantity of said coke being 1 to 30% by weight of said alumina particles, and the pore volume and the specific surface area of said catalyst being 0.05 to 1.5 cm$^3$/g and 1 to 500 m$^2$/g, respectively, under a hydrogen partial pressure of 1 to 50 kg/cm$^2$ and at a temperature of 450° to 700° C.

2. The process for hydrodealkylation as claimed in claim 1, wherein the catalyst is produced by causing coke to deposit on porous alumina particles having a pore volume of 0.1 to 1.5 cm$^3$/g and a specific surface area of 5 to 500 m$^2$/g by decomposition of a hydrocarbon on the particles.

3. The process for hydrodealkylation as claimed in claim 2, wherein the decomposition of a hydrocarbon is by means of thermal cracking, or by means of hydrodealkylation when the hydrocarbon is an alkylaromatic hydrocarbon.

4. The process for hydrodealkylation as claimed in claim 1, wherein said catalyst has been heated in an atmosphere comprising molecular oxygen and/or steam at a temperature of 600° to 1000° C.

5. The process for hydrodealkylation as claimed in claim 1, wherein it has a weight mean diameter of 25 to 250 μm and an apparent bed density of 0.3 to 1.5 g/cm$^3$.

6. The process for hydrodealkylation as claimed in claim 1 wherein the hydrodealkylation step is conducted in a reaction zone housing a fluidized bed of catalyst particles for hydrodealkylation, the catalyst particles with coke deposited thereon as the result of the hydrodealkylation are withdrawn from the reaction zone, treating the catalyst particles withdrawn in a fluidized state in another reaction zone with molecular oxygen and/or steam thereby to lower the coke content to a level of 1 to 30% by weight of the alumina, and returning the catalyst particles thus treated to the hydrodealkylation step.

7. The process for hydrodealkylation as claimed in claim 1, wherein the hydrodealkylation step is conducted in a reaction zone housing a fluidized bed of catalyst particles for hydrodealkylation.

* * * * *